US012031906B2

United States Patent
Barrett

(10) Patent No.: US 12,031,906 B2
(45) Date of Patent: Jul. 9, 2024

(54) METHOD AND APPARATUS FOR MAPPING DISTRIBUTION OF CHEMICAL COMPOUNDS IN SOIL

(71) Applicant: S4 Mobile Laboratories, LLC, Akron, OH (US)

(72) Inventor: Linda Barrett, Fairlawn, OH (US)

(73) Assignee: S4 Mobile Laboratories, LLC

( * ) Notice: Subject to any disclaimer, the term of this patent is extended or adjusted under 35 U.S.C. 154(b) by 0 days.

(21) Appl. No.: 18/331,370

(22) Filed: Jun. 8, 2023

(65) Prior Publication Data

US 2023/0400408 A1 Dec. 14, 2023

Related U.S. Application Data

(60) Provisional application No. 63/366,028, filed on Jun. 8, 2022.

(51) Int. Cl.
*G01N 21/3563* (2014.01)
*G01N 21/359* (2014.01)
(Continued)

(52) U.S. Cl.
CPC ....... *G01N 21/3563* (2013.01); *G01N 21/359* (2013.01); *G01N 21/8507* (2013.01);
(Continued)

(58) Field of Classification Search
CPC ............. G01N 21/3563; G01N 21/359; G01N 21/8507; G01N 33/24; G01N 2021/855;
(Continued)

(56) References Cited

U.S. PATENT DOCUMENTS 5,128,882 A 7/1992 Cooper et al.
5,170,056 A 12/1992 Berard et al.
(Continued)

FOREIGN PATENT DOCUMENTS

CA 3039881 A1 4/2018
CN 107144535 A 9/2017
(Continued)

OTHER PUBLICATIONS

Kim, Tae Woon, International Search Report; Korean Intellectual Property Office; PCT/US2023/068120; dated Sep. 19, 2023; 4 pages.
(Continued)

*Primary Examiner* — Dominic J Bologna
(74) *Attorney, Agent, or Firm* — Emerson Thomson Bennett; Daniel A. Thomson

(57) ABSTRACT

A method for mapping distribution of chemical compounds in soil is described herein including inserting a probe into the soil at multiple locations, obtaining spectroscopic data regarding the soil, sampling a core of soil adjacent to the probe locations, dividing the core into multiple depth increments, analyzing the core samples, matching each core sample with a corresponding depth increment of the probe insertions, obtaining data from the probe insertions, dividing the probe insertion data into training, validation, and test categories, resampling spectral variables from the probe insertion data to a wavelength interval longer than a native wavelength interval of an associated spectrometer, normalizing the probe insertion data on a spectrum by spectrum basis, utilizing a machine learning normalization algorithm, standardizing the spectral variables to a common scale by removing a mean and scaling to unit variance, and choosing a model utilizing the test set.

19 Claims, 7 Drawing Sheets

Figure 1:
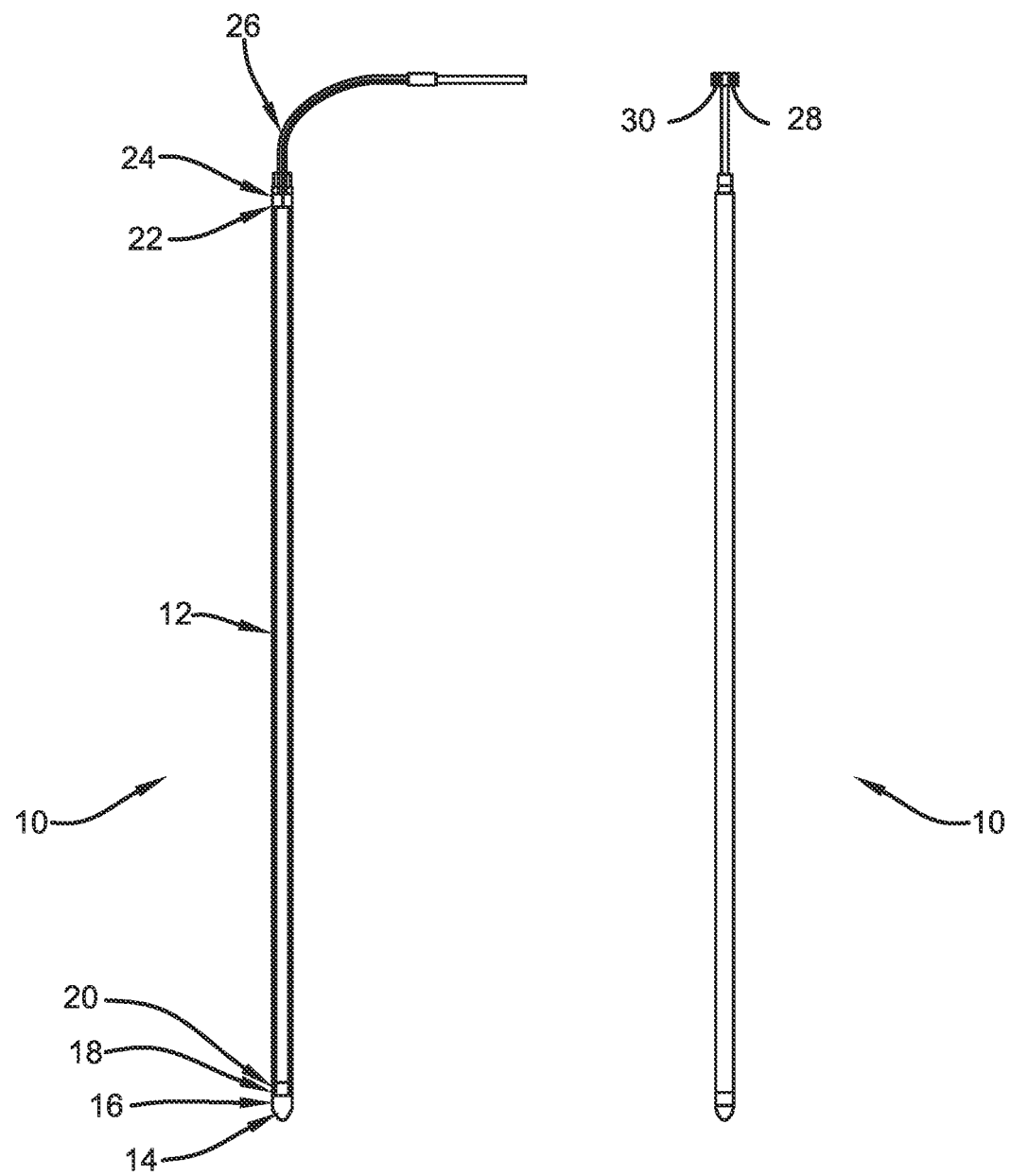

(51) Int. Cl.
*G01N 21/85* (2006.01)
*G01N 33/24* (2006.01)
*G01S 19/26* (2010.01)

(52) U.S. Cl.
CPC .............. *G01N 33/24* (2013.01); *G01S 19/26* (2013.01); *G01N 2021/855* (2013.01); *G01N 2201/0636* (2013.01); *G01N 2201/0638* (2013.01); *G01N 2201/08* (2013.01)

(58) Field of Classification Search
CPC ... G01N 2201/0636; G01N 2201/0638; G01N 2201/08; G01S 19/26
See application file for complete search history.

(56) References Cited

U.S. PATENT DOCUMENTS

| | | |
|---|---|---|
| 5,461,229 A | 10/1995 | Sauter et al. |
| 5,635,710 A | 6/1997 | Reed et al. |
| 5,739,536 A | 4/1998 | Bucholtz et al. |
| 6,018,389 A | 1/2000 | Kyle et al. |
| 6,097,785 A | 8/2000 | Elam |
| 6,147,754 A | 11/2000 | Theriault et al. |
| 9,285,501 B2 * | 3/2016 | Christy .............. G01N 21/3563 |
| 10,321,623 B1 * | 6/2019 | Maxton .................. G01N 21/31 |
| 10,337,159 B2 | 7/2019 | Morgan et al. |
| 2009/0166520 A1 | 7/2009 | Tuli et al. |
| 2013/0018587 A1 | 1/2013 | Clark et al. |
| 2013/0026354 A1 | 1/2013 | Troxler |
| 2014/0012504 A1 * | 1/2014 | Ben-Dor ................. G01N 33/24 702/2 |
| 2017/0370064 A1 * | 12/2017 | Morgan ................... G01J 3/108 |
| 2021/0364462 A1 * | 11/2021 | Orangi .................... G01K 1/143 |
| 2022/0349815 A1 * | 11/2022 | Nagel ...................... B65G 17/20 |

FOREIGN PATENT DOCUMENTS

| | | |
|---|---|---|
| CN | 109342260 A | 2/2019 |
| CN | 111880206 A | 11/2020 |
| CN | 113167780 A | 7/2021 |
| EP | 1264170 B1 | 4/2009 |
| NL | 2017647 B1 | 10/2016 |
| WO | WO2020056506 A1 | 3/2020 |
| WO | 2020-160605 A1 | 8/2020 |

OTHER PUBLICATIONS

Kim, Tae Woon; International Written Opinion; Korean Intellectual Property Office; PCT/US2023/068120; dated Sep. 19, 2023; 6 pages.

* cited by examiner

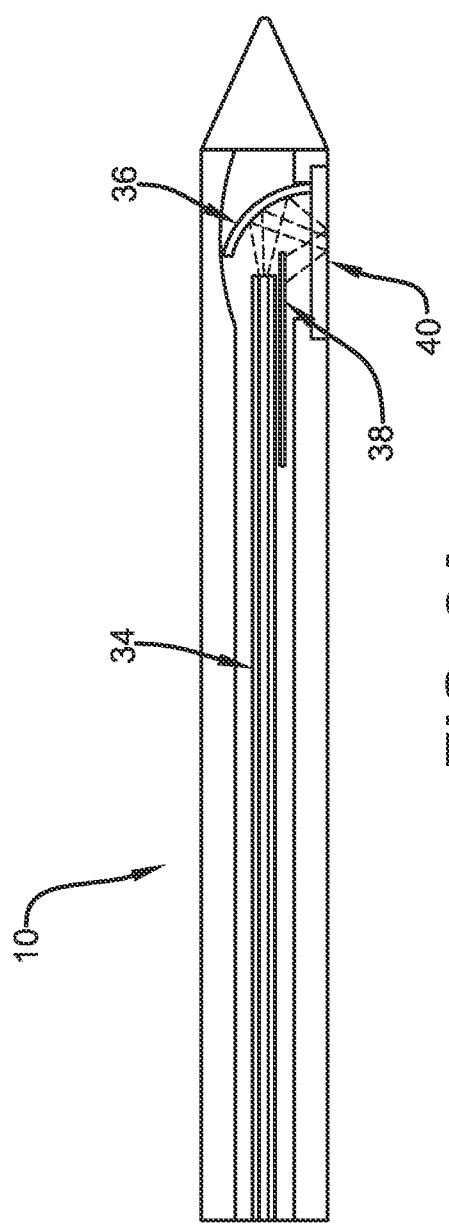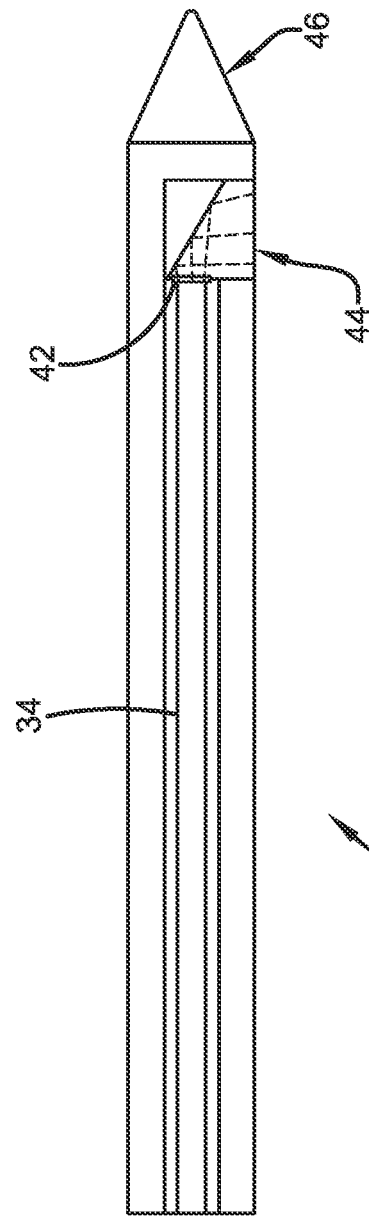

METHOD AND APPARATUS FOR MAPPING DISTRIBUTION OF CHEMICAL COMPOUNDS IN SOIL

This application claims priority to provisional patent application Ser. No. 63/366,028, filed Jun. 8, 2022, the contents of which are incorporated herein by reference. The present teaching is directed to detecting chemical compounds in soil. More specifically, the present teaching is directed to the use of a spectroscopic probe to detect chemical compounds in soil.

I. BACKGROUND

In situ shallow sub-surface soil spectroscopy (hereafter "S4") is an analytical prospection technique that records optical spectra of subsurface soil using a probe mounted on a mobile instrument where the probe is connected to visible-near infrared (vis-NIR) spectrometers with optical fibers.

There are various types of in situ spectroscopy that are used in a wide variety of applications. In situ chemical testing of soils and residues (i.e., without excavation or extensive coring) remains methodologically underdeveloped. The technique in rapid in situ soil analysis is portable XRF (X-ray fluorescence). In-situ handheld XRF has seen a wide variety of applications such as mining, lead paint testing, and for heavy metal mapping of soil. The Niton XRF analyzers distributed by Fisher Scientific are one of the popular instruments for in situ soil analysis. Another emerging in situ soil analysis technique is portable LIBS (Laser-induced breakdown spectroscopy). In-situ soil analysis for $Cu^{11}$, $Cr^{12}$, $Pb^{13}$ and other soil pollutants have been performed with portable LIBS in the recent years. Portable vis-NIR spectroscopy, such as the Veris P4000, has been used in situ for over two decades despite its shortcoming in the accuracy of soil properties quantification.

In soils and sediments, large amounts of soil organic carbon (SOC) mark reducing conditions. As dark sediment colors are good predictors for high-SOC zones, they indicate hot spots of biogeochemical turnover and microbial activity. Traditionally, obtaining the sediment color or SOC at depth requires costly core sampling, resulting in poor horizontal resolution and related uncertainty caused by interpolation.

Etatloning is an effect which takes place when light reflects between two flat surfaces, separated by a small distance comparable to the wavelength of the incident light. Such an effect is produced when the light goes from a medium of one index of refraction (e.g., glass or sapphire) to another with a different index of refraction air). A fraction of the light is reflected from the interface by the Fresnel effect and interferes with the light from the second surface.

In optics, an index-matching material is a substance, usually a liquid, cement (adhesive), or gel, which has an index of refraction that closely approximates that of another object (such as a lens, material, fiber-optic, etc.). An index-matching material may be used in conjunction with pairs of mated connectors or with mechanical splices to reduce signal reflected in the guided mode (known as return loss). Without the use of an index-matching material, Fresnel reflections will occur at the smooth end faces of a fiber unless there is no fiber-air interface or other significant mismatch in refractive index.

Since 1850, soils have lost an estimated 78 Gt of carbon, primarily due to cultivation. This loss of soil carbon represents a significant portion of greenhouse gas emissions and has resulted in the degradation of agricultural soil quality worldwide. Using practices that restore carbon, such as no-till farming, carbon can be sequestered in the soil. Carbon sequestration has the potential to offset fossil fuel emissions by 0.4 to 1.2 gigatons of carbon per year, or 5 to 15 percent of global fossil fuel emissions.

Under a cap-and-trade system, farmers and landowners would be paid for adopting carbon-sequestration techniques, provided their increases in carbon can be measured, monitored, and verified. There are at least two major hurdles in accounting for soil carbon. One, carbon increases due to farming practice changes are very small—a 10% increase in carbon over ten years is typical. Second, carbon varies widely within a field, even within a few meters. Key to soil health is maintenance of the soil's organic carbon content. Carbon credit markets incentivize practices that increase the soil organic carbon content so that the resulting carbon sequestration will contribute to stabilization of atmospheric carbon dioxide levels. However, such markets are not feasible without accurate and cost-effective means for verifying the soil organic carbon stock.

A cost-effective method of measuring SOC is significant because voluntary carbon credit markets are growing rapidly, as are markets that reward sequestration of carbon in the soil. However, a major hurdle to the establishment of a functioning carbon credit market is the lack of inexpensive and accurate protocols for measurement of SOC stock. Uncertainty in verification of SOC stock depresses the price of soil carbon credits, threatening the market viability.

Baseline SOC stock is challenging to determine, because even within an apparently uniform agricultural field, there can be high spatial variability. Change detection is even more demanding because SOC is only modestly impacted by agricultural practices, and therefore management-induced increase in carbon over the scale of years is small relative to baseline. Large sample numbers and careful sampling design are required to achieve the precision necessary to measure such small increases. To limit project cost, many protocols only require sampling to a depth of 15 or 30 cm. Yet significant SOC can exist to much greater depths, and there is a good rationale for measuring SOC to at least 100 cm.

Current measurement, reporting, and verification (MRV) protocols encompass a range of methods for estimation of SOC stock, including direct and indirect measurements, estimation by modeling, and hybrid approaches. Model-based approaches often have unacceptable uncertainties exceeding 600% at the site scale. At the field scale, 3 to 5 years are required for changes to be sensed using existing direct measurement methods, which delays payments for credits. Yet any credits awarded must be based on accurate estimate of carbon net sequestration.

Direct measurement protocols typically call for field sampling and laboratory analysis of soil cores, but labor costs and laboratory fees make the process prohibitively expensive given the large number of samples required to reach an acceptable precision. Validation of C sequestration should use a volumetric measurement (mass per area to a given depth), termed SOC stock, which is derived from laboratory measurements of SOC concentration (mass per mass of soil) and bulk density (BD), which are measured separately.

A standard normal variate is a normal variate with mean $\mu=0$ and standard deviation $\sigma=1$ with a probability density function is $f(z)=1/(2\pi)^{1/2} e^{-z^2/2}$. The variate would take a value between 0 and z. This can be read from the table of areas under Standard Normal Curve. The area from 0 to z can be found to any corresponding z from this table. Let X is a normal variate with mean $\mu$ and standard deviation $\sigma$.

Then $Z=(X-\mu)/\sigma$ is a Standard Normal Variate. Hence the Standard Normal Variate can be used to find the probability regarding X. The expected value of a standard normal variable X is $E[X]=0$ and the variance is $Var[X]=1$. The characteristic function of a standard normal random variable X is: $\phi x(t)=\exp((-\frac{1}{2})t^2)$.

A Savitzky-Golay filter is a digital filter that can be applied to a set of digital data points for the purpose of smoothing the data, that is, to increase the precision of the data without distorting the signal tendency. This is achieved, in a process known as convolution, by fitting successive sub-sets of adjacent data points with a low-degree polynomial by the method of linear least squares. When the data points are equally spaced, an analytical solution to the least-squares equations can be found, in the form of a single set of "convolution coefficients" that can be applied to all data sub-sets, to give estimates of the smoothed signal, (or derivatives of the smoothed signal) at the central point of each sub-set. The data consists of a set of points $\{x_j, y_j\}$, $j=1, \ldots, n$, where $x_j$ is an independent variable and $y_j$ is an observed value. They are treated with a set of m convolution coefficients, $C_i$, according to the expression $$Y_j = \sum_{i=\frac{1-m}{2}}^{\frac{m-1}{2}} C_i\, y_{j+i},\ \frac{m+1}{2} \le j \le n - \frac{m-1}{2}$$

For example, for smoothing by a 5-point quadratic polynomial, m=5, i=−2, −1, 0, 1, 2 and the jth smoothed data point, $Y_j$, is given by $$Y_j = \frac{1}{35}(-3y_{j-2} + 12y_{j-1} + 17y_j + 12y_{j+1} - 3y_{j+2})$$

where, $C_{-2}=-3/35$, $C_{-1}=12/35$, etc.

Recursive Feature Elimination, or RFE for short, is a feature selection algorithm. A machine learning dataset for classification or regression is comprised of rows and columns, like an excel spreadsheet. Rows are often referred to as samples and columns are referred to as features, e.g. features of an observation in a problem domain. Feature selection refers to techniques that select a subset of the most relevant features (columns) for a dataset. Fewer features can allow machine learning algorithms to run more efficiently (less space or time complexity) and be more effective. Some machine learning algorithms can be misled by irrelevant input features, resulting in worse predictive performance. RFE is a wrapper-type feature selection algorithm. This means that a different machine learning algorithm is given and used in the core of the method, is wrapped by RFE, and used to help select features. This is in contrast to filter-based feature selections that score each feature and select those features with the largest (or smallest) score. Technically, RFE is a wrapper-style feature selection algorithm that also uses filter-based feature selection internally. RFE works by searching for a subset of features by starting with all features in the training dataset and successfully removing features until the desired number remains. This is achieved by fitting the given machine learning algorithm used in the core of the model, ranking features by importance, discarding the least important features, and re-fitting the model. This process is repeated until a specified number of features remains. A five-fold cross-validation (CV) is a process when all data is randomly split into k folds, in one case k=5, and then the model is trained on the k−1 folds, while one fold is left to test a model. This procedure is repeated k times.

II. SUMMARY

A thermally resistant, all-fiber-optic probe is described in the present teaching, which allows for 3D mapping of soil organic carbon.

An all-fiberoptic probe allows for all of the active components of the systems, including the light source and the spectrometers, remain above ground. The light from the light source is conducted through fiber optics to the distal end of the probe, which is inserted into the ground to illuminate the soil at its in situ location. Some of the light that is diffusely reflected from the soil is conducted by optical fibers from the distal end up to the spectrometers that are located above ground. The all-fiberoptic design means that the probe to be inserted into the ground can be made smaller in diameter, requiring less force to insert it into the ground and therefore smaller, lighter equipment to implement the technology as compared to competing technology for which the light source is contained in the probe head, which then has a larger cross section and requires much more insertion force.

Several aspects of the probe enable it to operate under a wide range of environmental conditions. Over a wide range of operating temperatures (e.g., 0° C. to 40° C.), the differential thermal expansion of the optical fibers and the metal probe puts stress on the materials in the light path, from the distal end where the light hits the soil, up to any point where the optical fibers are fixed to the probe tube. The entirety of the optical paths through the probe tube utilize soil state, index-match material, which avoids air gaps. If the stress on the optical materials is too great, then the optical materials may pull apart, leaving an air gap. An air gap can cause etaloning, a phenomenon that causes wavelength-dependent signals that would obscure the desired spectroscopic signal. The present teaching employs a floating prism, connected to the adjacent optical parts by an index-matching fluid, mounted in such a way that the differential thermal expansion can be accommodated without creating significant stress on the components. The prism is spring-loaded to keep it in contact with the adjacent optical components.

The present teaching yields spectroscopic data at a 3-dimensional array of locations in the soil. From each spectrum the amount of certain analytes is determined at that location in the soil. One analyte of particular interest is soil organic carbon (SOC), but other analytes might also be determined, depending on the application. The result for each analyte determined from the spectra is a 3-dimensional map of the analyte's concentration in the soil. The 3-D map can then be integrated over a particular parcel of land to give the total amount of that analyte on that parcel of land. Useful applications of such data include determination of the total SOC on a parcel of land for the purpose of allocating carbon credits. The 3-D map of SOC, or of certain agricultural nutrients, can be used for precision agricultural husbandry, including maximization of crop yields, minimization of the cost of inputs, and optimization of tilling practices and crop rotations.

It is impossible to determine the true absolute SOC stock for a site, no matter the protocol or technology, because all are subject to sampling and measurement errors. It is therefore good practice to report both the average value obtained and an uncertainty measurement. Error and uncertainty can be associated with (1) single samples (measurement of SOC in a given sample); (2) cores or profiles (measurement of SOC content from the surface to the measurement depth at one point); and (3) plots or sites (determination of SOC stock for the entire plot). The overall uncertainty of a given protocol must be evaluated on the basis of all three categories.

For protocols based on field sampling and laboratory measurement, analytical uncertainty at the single sample level is assumed to be negligible, but in fact may be substantial. Uncertainty is derived from sample handling, subsampling, and preparation as well as analytical procedures. At the soil profile level, in most cases only two samples are taken: from 0-10 cm and from 10-30 cm. For each depth increment, the samples are homogenized and the SOC concentration of a very small representative portion is determined. Incomplete homogenization contributes to uncertainty, and also eliminates information about variability with depth.

At the plot level, many protocols require sampling using strata that are uniform with respect to known co-variates, and compositing of samples to control costs. Compositing allows the measurement to represent the average value for an area, but information about spatial variability is lost. Inadequate mixing of composite samples is a significant source of uncertainty. Increasing the number of strata decreases plot-level uncertainty, but also increases the total number of samples. Nevertheless, even the minimum number of samples required can be cost-prohibitive. For a 50 ha farm, power analyses indicate that the number of samples required to detect even a high absolute change of 0.1% C (e.g., from 1.0% C to 1.1% C) can be around 25 per ha, and lower increases of 0.05% in SOC concentration, as might be expected over five years, would require many more than 50 per ha.

When considering a replacement for a de facto standard, by definition the alternative cannot be as accurate as the standard because it is calibrated against the standard and incurs statistical error. Any errors in the standard will be present in the calibration and reduce the accuracy of the alternative. However, the precision of the alternative can be better than the standard with the proper sampling protocol. With the present teaching, a probe insertion can be done rapidly (<two minutes with the current prototype), no sample handling or processing is required, and additional insertions do not incur additional laboratory analysis costs. Therefore, for similar cost one can take many more measurements using the present teaching than would be possible using laboratory-based techniques, both within each sampled profile (e.g., about 30 measurements per profile, as opposed to one or two) and the number of profiles within each plot. Increasing the number of sampled profiles decreases the uncertainty associated with per-sample, soil profile, and plot level measurements (see Shuo Li, et al. with respect to portable VNIR spectroscopy). In addition, because there is no compositing of samples, the present teaching retains information about spatial variability, and therefore can also be used to produce a detailed 3D map of SOC content over the site.

One aspect of the present teaching consistently achieves a precision of better than 0.3 Mg C per hectare for soil organic carbon stock determination, sufficient for verification in the carbon credit market. The record of model performance with respect to the co-variates rubric will demonstrate that these high accuracy levels are achievable in commercial application throughout the target area without the need for large numbers of additional calibration samples. Similar to an independent variable, a covariate is complementary to the dependent, or response, variable. A variable is a covariate if it is related to the dependent variable. A rubric is an attempt to communicate expectations of quality around a task.

The present teaching describes a mobile field unit with a visible and near infrared (VNIR) spectroscopic probe and a load cell for measuring probe insertion force. As the unit moves across a target area, the probe is pushed into the soil at intervals, measuring light reflected from a column of soil immediately adjacent to the probe. These data, and the location and force required to insert the probe, are converted into a 3D map of subsurface volumetric soil organic carbon (SOC) stock, as well as point measurements of SOC concentration and soil bulk density (BD). These maps can be used to promote soil health and for soil carbon credit accounting.

One advantage of the present teaching is that it can produce the SOC stock estimates directly (as well as SOC concentration and BD), without extra time, expense, or effort. Additionally, it is smaller and more maneuverable than existing probe-based instruments discussed below, and can map at finer spatial scales and with a significant reduction in cost and effort over current protocols.

The present teaching is designed to rapidly and cost-effectively determine SOC stock to a depth of up to 90 cm. The unique all-fiber-optic design allows a small diameter (<14 mm) probe that results in a light, maneuverable field unit that can attain satisfactory insertion depths. A single operator can use it in heavy vegetative cover and on rugged terrain. It returns preliminary estimates of SOC stock in real time, eliminating the delays inherent in analysis of laboratory samples and allowing refinements to importance sampling protocols as samples are acquired. More accurate maps are obtained after calibration samples are analyzed. It is to be understood, however, that the present teaching is not limited to analysis and determination of SOC, but can be used to determine any chemical compound. In one aspect of the present teaching, the probe has a diameter of less than 30 mm, in another aspect the probe has a diameter of less than 25 mm, and in another aspect the probe has a diameter of less than 20 mm. In one aspect of the present teaching, the probe is inserted at a maximum insertion force of about 240 pounds (1067.57 N) or less. In another aspect, the probe is inserted at a maximum insertion force of about 400 pounds (1779.29 N) or less. In another aspect, the probe is inserted at a maximum insertion force of about 500 pounds (2224.11 N) or less. In one aspect of the present teaching, the shaft has a diameter of less than 30 mm, in another aspect the shaft has a diameter of less than 25 mm, in another aspect the shaft has a diameter of less than 20 mm, and in another aspect the shaft has a diameter of less than 15 mm.

Still other benefits and advantages of the present subject matter will become apparent to those skilled in the art to which it pertains upon a reading and understanding of the following detailed specification.

III. BRIEF DESCRIPTION OF THE DRAWINGS

The present teachings are described hereinafter with reference to the accompanying drawings.

Figure 3:
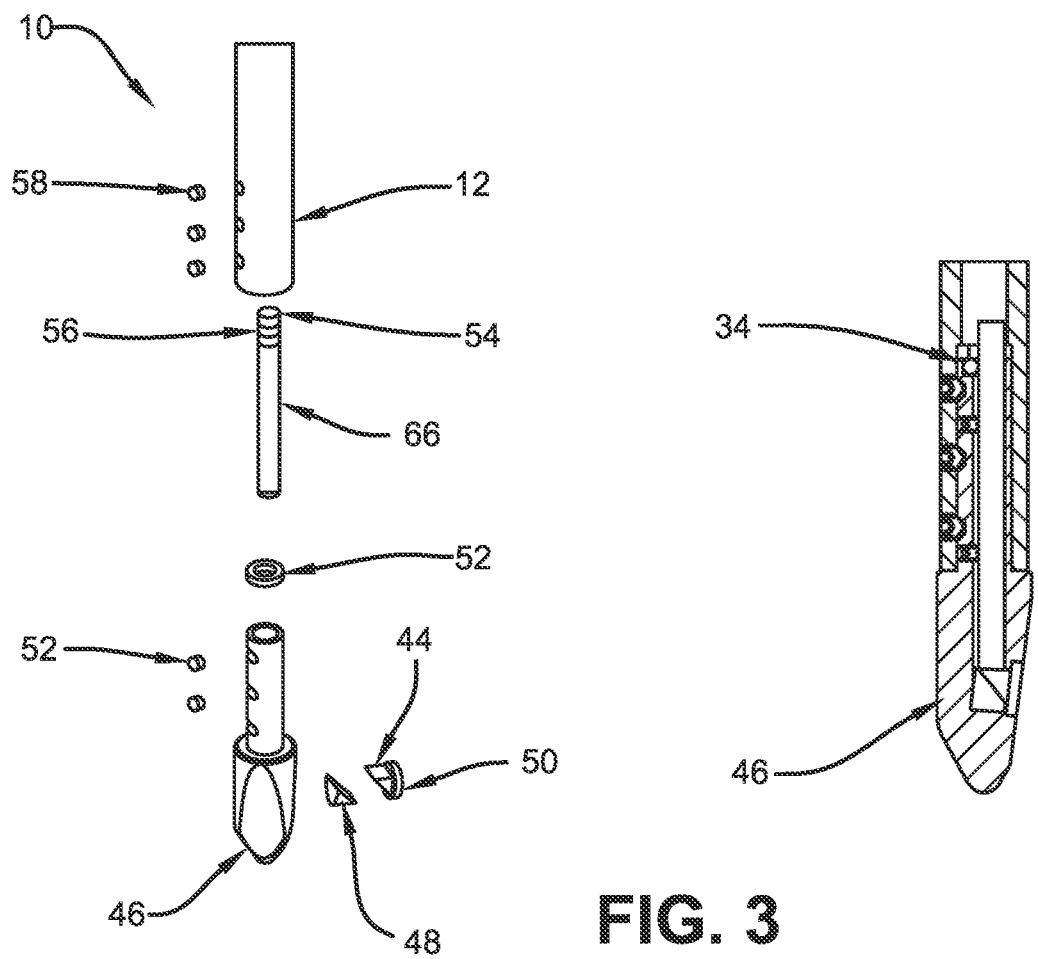
Figure 4A:
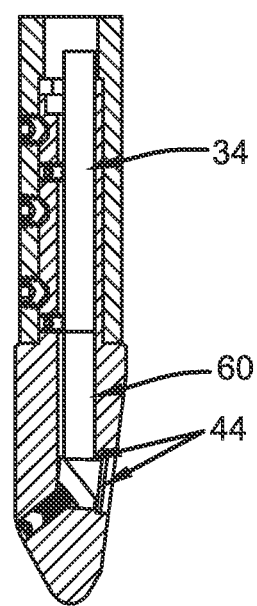
Figure 4B:
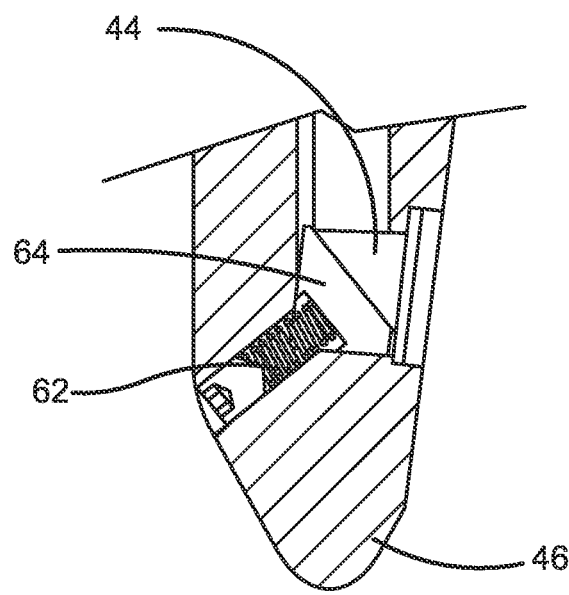
Figure 5:
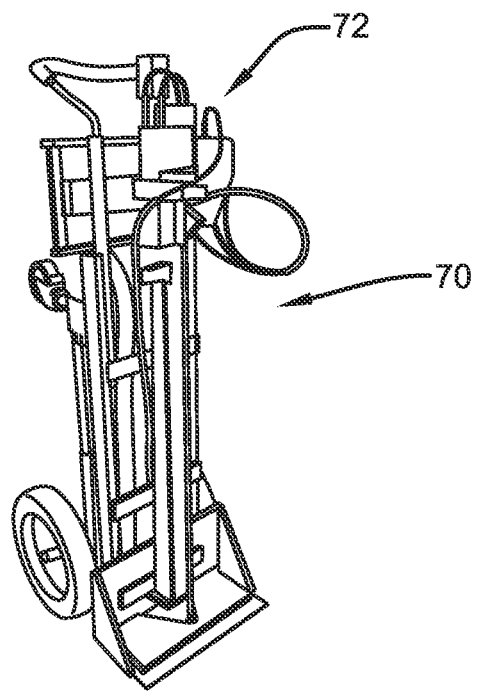
Figure 6:
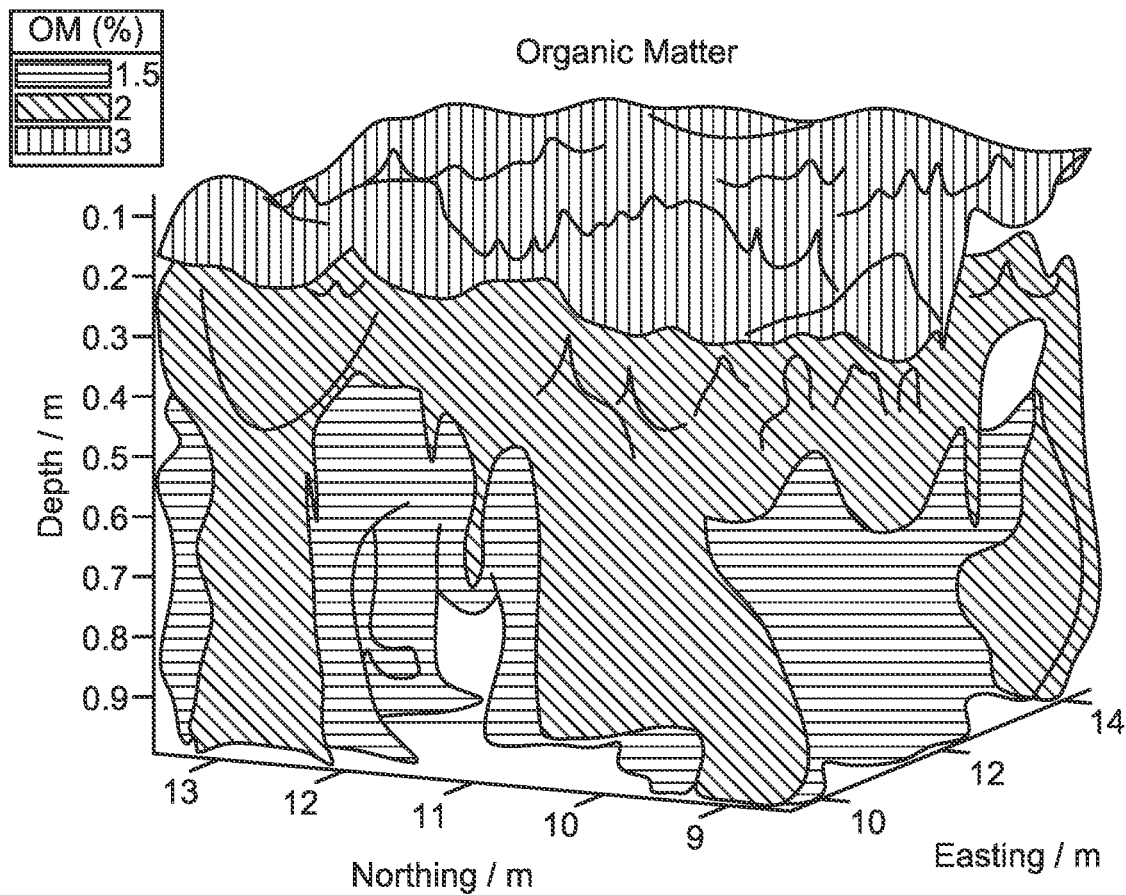
Figure 7:
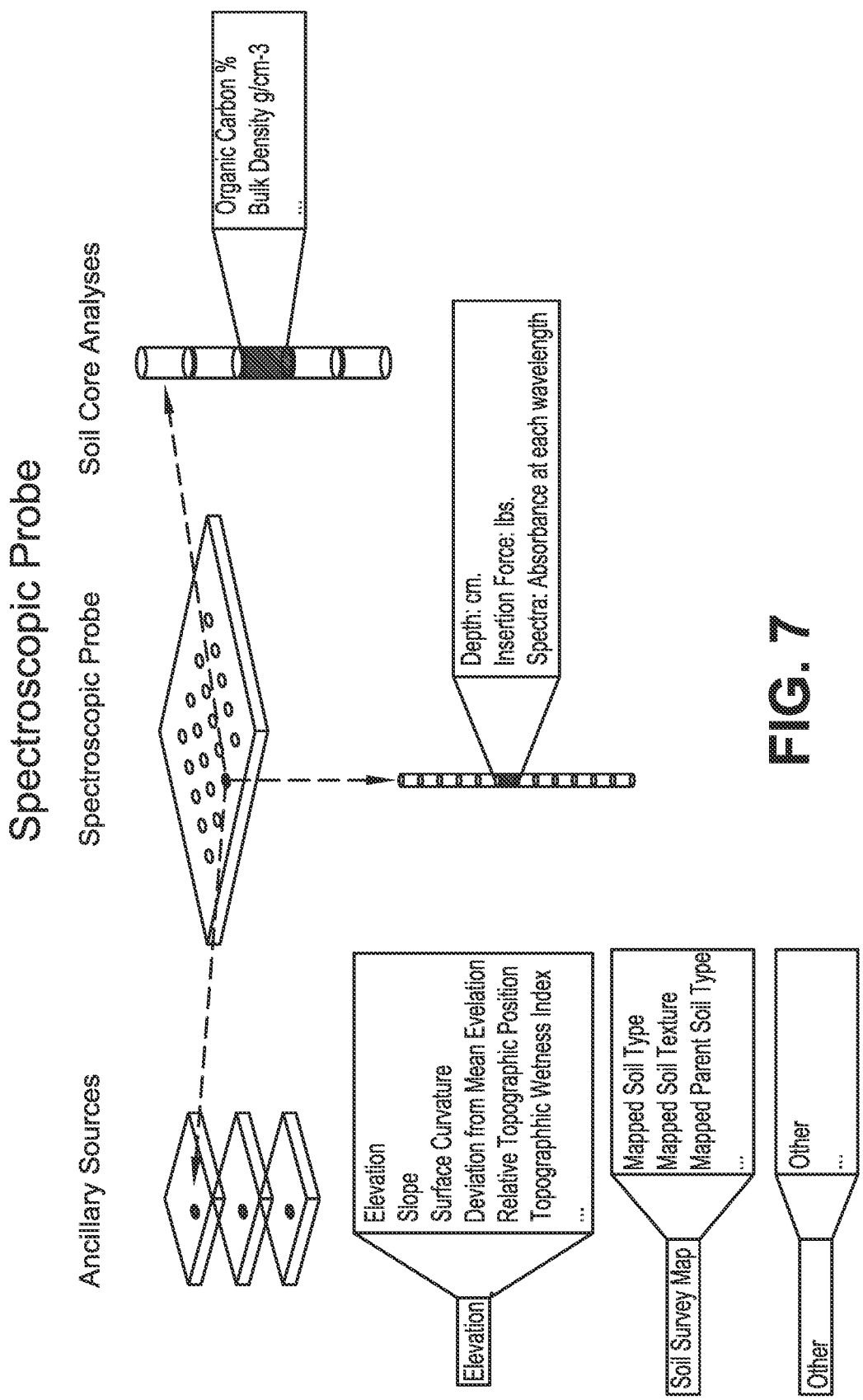
Figure 8:
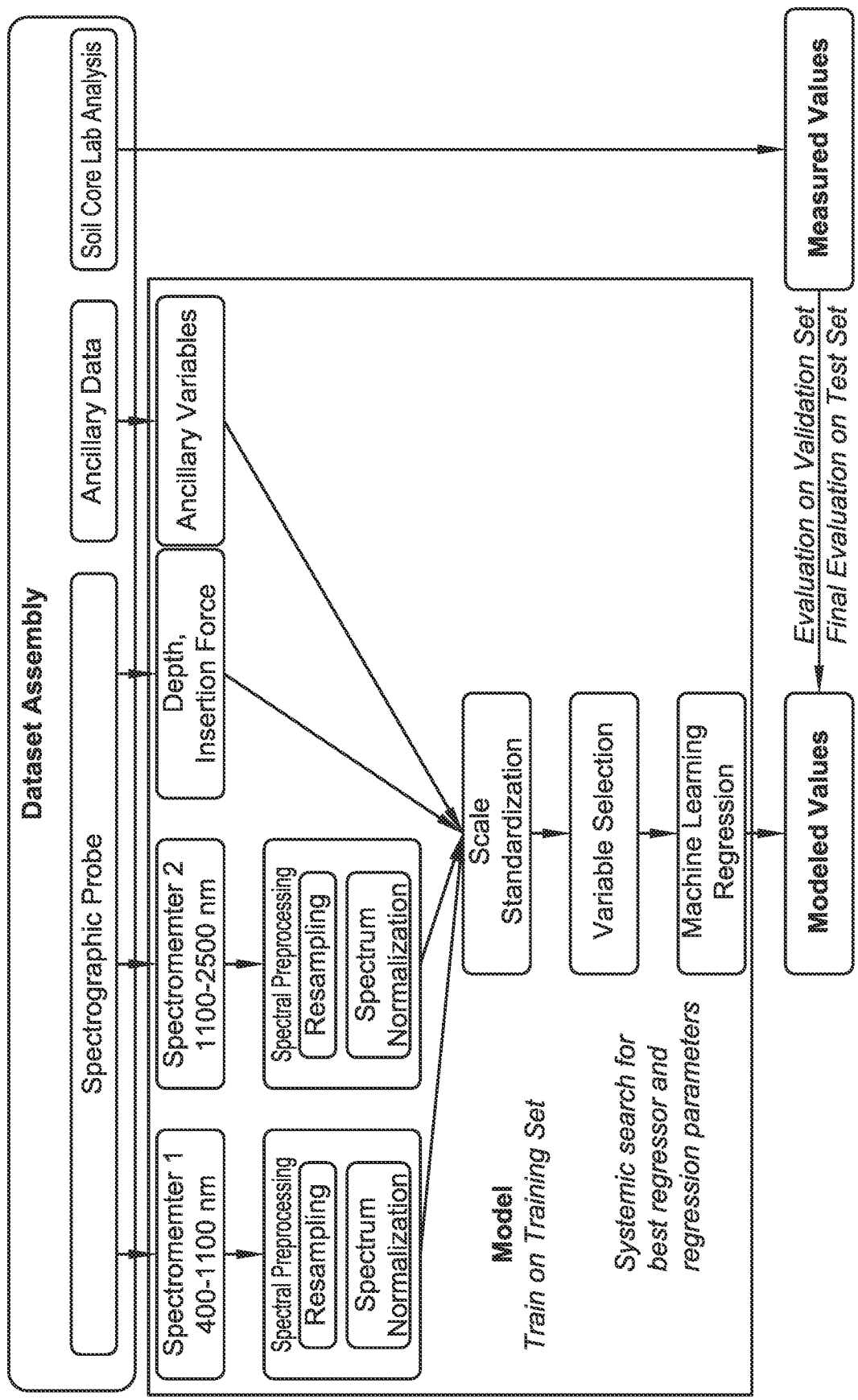

FIG. 1 shows a spectrometer probe;
FIG. 2A shows a cross-section of the probe;
FIG. 2B shows a cross-section of the probe;
FIG. 3 shows an exploded view of the probe;
FIG. 4A shows a cross-section of the probe;
FIG. 4B shows an enlarged cross-section of the probe end;
FIG. 5 shows a prospective view of a probe carrier;

FIG. 6 shows a 3D map;
FIG. 7 shows a data set assembly; and
FIG. 8 shows a model for training.

IV. DETAILED DESCRIPTION

With reference now to FIG. 1, spectrometer probe 10 is shown having an outer sleeve 12, a protector endcap 14, a spacer tab 16, a probe sample window 18, a light reflection insert 20, a top spacer tab 22, a protector tube top cap 24, near-infrared (NIR) probe cable 26, read fiberoptic cable 28, and light source fiberoptic cable 30. FIG. 2A shows a cross section of probe 10 having fiber bundle 34, concave mirror 36, backscatter baffle 38, and sapphire window 40. FIG. 2B shows a cross section of probe 10 having fiber bundle 34, index-matching elastomer 42, sapphire prism 44, and penetration cone 46. FIG. 3 shows an exploded view of the probe 10 showing the outer sleeve 12, the sapphire prism 44, the penetration cone 46, support prism 48, sapphire window 40, set screws 52, inner sleeve 66, inner sleeve top 54, grooves 56, and set screws 58. FIG. 4A shows the fiber bundle 34, the sapphire prism 44, and epoxy 60 to bond the fibers in the tube. FIG. 4B shows the penetrating cone 46, the sapphire prism 44, a prism support 64, and spring 62.

With continuing reference to FIGS. 1-4B, the read fiberoptic cable 28 and light source fiberoptic cable 30 are located next to each other, but combine to form the fiberoptic bundle 34 that passes through the NIR probe cable 26 and down through the probe 10 inside outer sleeve 12. The NIR probe cable 26 is held in place by top spacer tab 22 and protector tube top cap 24. The fiber bundle 34 extends through the inner sleeve 12 to the protector end cap 14. At the end of the probe 10, near the penetration cone 46, there is the spacer tab 16, the probe sample window 18, and the light reflection insert 20. In one aspect of the present teaching, as shown in FIG. 2A, the probe 10 has a concave mirror 36, backscatter baffle 38, and sapphire window 40. Light from the light cable 30 travels through the fiber bundle 34, reflects off of the mirror 36 and travels through the sapphire window 40. The backscatter baffle 38 helps prevent backscatter from the light.

With continuing reference to FIGS. 1-4B, the probe 10 does not experience etaloning because of the solid-state optical path along with the index-matching elastomer 42 between the prism 44 and the prism support 64. The probe 10 has an inner sleeve 66 inside the outer sleeve 12. Near the inner sleeve top 54, grooves 56 have been cut into the inner sleeve 66 in order to fill with epoxy for better stabilization. The set screws 52, 58 also help stabilize the probe 10. In one aspect of the present teaching, a spring 62 is added behind the prism support 64 in order to create pressure, and allow fluctuation without having an air gap. Air gaps create wavelength interference and create spurious data. Additionally, index-matching elastomer 42 is utilized such that the prism 44 is completely surrounded by, and floating in, the index-matching elastomer fluid 42. The prism 44 is flush with the surface of the probe 10 and sealed. In one aspect of the presenting teaching the index-matching elastomer can be a silicone elastomer, but it is to be understood that any index-matching material can be chosen using sound engineering judgment. In one aspect of the present teaching, the spring 62 could be substituted with an elastically deformable material, such that pressure and fluctuation are still accomplished without using a spring.

With continuing reference to FIGS. 1-5, the probe 10 is connecting to a portable carrier 70, which has an actuator 72. The actuator 72 pushes the probe 10 into the ground. The penetrating cone 46 is designed to provide better ease for ground penetration. The fiber bundle 34 takes and carries the light to and from the soil. The light is analyzed using diffuse reflective spectroscopy to detect various components in the soil. The probe 10 uses a reflective prism 44 and a side-looking probe sample window 18 to analyze the soil. The fiber bundle 34 can be anchored to the penetrating cone 46 at a single point instead of multiple points. The probe 10 can be made of stainless steel. In one aspect of the present teaching, spectra of the soil are taken every 2.5 cm to measure soil organic carbon. The spectra are thus taken at various depths of the soil. Light passes through the sapphire window 40 to strike the soil. Some light ($I(\lambda)$) is diffusely reflected back to reach the spectrometer (not shown), which separates the different wavelengths ($\lambda$) of the light. The intensity of the reflected light from the soil ($I(\lambda)$) is compared to the light reflected from a white test blank ($I_0(\lambda)$). At each $\lambda$, the effective absorbance is calculated as $A(\lambda)=\log_{10}[I_0(\lambda)/I(\lambda)]$. A plot of the absorbance $A(\lambda)$ versus wavelength $\lambda$ constitutes a spectrum and is the input data for the present teaching. In one aspect of the present teaching, the spectrometers are sensitive to the ranges 500-1100 nm, and 1100-2500 nm, which in tandem can sense nearly the entire visible and near infrared spectrum.

With continuing reference to FIGS. 1-5, a spectrometer (not shown) can be modular, above ground, and connected to the probe 10 with a fiberoptic connector. In one aspect of the present teaching, up to three spectrometer modules covering different wavelength regions could be connected via suitable wavelength splitter fiber cables.

With reference now to FIGS. 1-6, the total soil organic carbon can be determined using the above-referenced probe 10, by taking various samples at different depths and horizontal distances. Once the data is collected, a 3D map can be created to show the location of the soil organic carbon, and the relative concentration locations of the soil organic carbon.

With reference now to FIGS. 1-6, an algorithm is used to analyze all of the spectrometer data to create a 3D map of the soil organic carbon like the map shown in FIG. 6. The various concentrations can be shown in various colors using isosurfaces. 3D maps can be generated for many different chemicals aside from the soil organic carbon. The probe and spectrometers enable the rapid and accurate mapping of soil organic carbon in three dimensions.

For each site, the probe insertion locations for which soil property data existed were randomly divided into training (60%), validation (20%), and test (20%) sets. All depth increments of a probe insertion were placed together into a set. The training set was used to develop the model, and the validation set was used to routinely check model performance. The test set was used to evaluate performance of the final model on novel data. Model fit was evaluated using root mean square error (RMSE). For comparison across sites, the ratio of performance to interquartile distance (RPIQ) was used, calculated by dividing the interquartile distance (difference between the $75^{th}$ and $25^{th}$ percentile values) by the RMSE. An RPIQ value >2.0 is often assumed to indicate excellent performance of a model. Also calculated was the coefficient of determination ($R^2$).

In the modeling step, spectral data were preprocessed by resampling and normalization using the standard normal variate. Ancillary data derived from digital elevation models using standard geomorphometric indices were also included as model input. All input variables were standardized by removing the mean and dividing by the standard deviation. The highly multicollinear variable set was reduced using recursive feature elimination with cross-validation, which excludes variables that are least informative for a regressor. A comprehensive search was conducted through a number of regressors, including support vector regression, partial least squares regression, random forest regression, and AdaBoost regression, and hyperparameter settings using five-fold cross-validation with the training set, choosing the model with the lowest RMSE of cross-validation. For SOC concentration separate models were developed for each site and for the combination of all sites. For some sites BD was also modeled using the same methods.

For SOC concentration and stock, metrics for individual sites and for site combinations exceeded the rule of thumb value of RPIQ≥2.0 on the test set for model performance. Metrics for the SOC per-sample models also generally met or exceeded the goal of $R^2 \geq 0.8$.

A per-sample model, applied to the full site data set, results in a lattice of measurements at each depth interval in each probe insertion. One method of visualizing the lattice is to map the soil property at regular depth intervals. Alternatively, the same data set can be used to visualize the soil property in 3D, as with the SOC concentration isosurfaces. Similar visualizations can be produced for any of the per-sample predicted soil properties.

SOC stock was estimated and mapped by summing the modeled per-sample SOC stock at each probe insertion to the maximum depth of the probe insertion.

Soil spectroscopy requires a database that widely samples the soil variability within the study area. The relationships between spectra and soil properties can be both spatially dependent and highly non-linear, and it is difficult to construct a calibration set that adequately reflects the immense variation found in soils. Establishment of the minimum change in per-site SOC stock detectable is tested, including a formal assessment of uncertainty associated with each sampling and modeling step.

A separate rubric can be developed for each target area. The target is that mean ΔRMSE will be better than −10%.

Data collection activities are organized around two different site types, intensive and extensive. Intensive sites are used to produce a single-site model, test accuracy and precision of SOC stock estimation, and create 3D maps of SOC stock, while the extensive sites are designed to efficiently extend calibration into previously uncovered portions of attribute space, even though in isolation they are not adequate for site-specific modeling or 3D mapping.

Initially, in a field of about 5 ha, probe insertions are in a grid pattern with a spacing of 15 m (~225 probe insertions and a density of ~50 ha$^{-1}$). A soil core is obtained at about 25% of the probe insertions (~60 cores, or 360 samples at 6 depths/core). A stratified random sampling design is used to determine the grid points at which cores are taken.

At each extensive site, between 20 and 100 ha in size, 15 probe insertions are obtained and the corresponding 15 cores (~90 samples at 6/core). Specific locations are chosen by stratifying the site to attribute space characteristics, and randomly sampling five points within each of three strata. Density depends on site size and strata distribution.

At both site types, the probe is inserted to a depth of about 90 cm or the maximum depth allowed by the soil. Spectral data are acquired at 1 cm intervals in the surface 15 cm, at 2.5 cm between 15 and 60 cm; and at 5 cm intervals thereafter. Soil cores (3.8 cm diameter) are extracted in a plastic liner to a depth of 1 m or as deep as reached by the probe. Cores are divided at 7.5, 15, 30, 45, and 60 cm. After outlier eliminating spectra are matched to the corresponding depth interval and averaged within the interval for modeling.

Samples are divided into training (60%), validation (20%), and test (20%) sets using stratified random selection. To maintain independence of the validation and test sets, all samples from a given soil core are assigned to the same set.

For any given site, the baseline is the model trained only on data collected at that site. Regional and global models, trained on data from broader geographical regions, will be evaluated with the usual accuracy metrics (RMSE, $R^2$, and RPIQ), but also by comparing the RMSE of validation of the broader model to that of the local site model. The primary metric is ΔRMSE, calculated as $((RMSE_a - RMSE_b)/(RMSE_b * 100))$ where $RMSE_a$ is the RMSE of the broader model applied to the individual site validation set and $RMSE_b$ is the RMSE of the site-specific model. ΔRMSE are continuously tracked at the site, regional, and global levels, with the target being ΔRMSE (broad vs. site) better than −10%. To track model performance on novel sites, the metric ΔRMSE is calculated for models developed both including and excluding data collected at the site from the training set, targeting ΔRMSE (excluded vs. included) better than −10%. To establish the minimum change in per-site SOC stock that is detectable using the present teaching, for each of the intensive sites a formal analysis of measurement uncertainty is conducted, with a target of precision sufficient to detect an increase of 0.3 Mg C ha$^{-1}$.

An exhaustive search is conducted through a variety of model types and hyperparameters, evaluating model performance using RMSE, $R^2$, and RPIQ. Also included are (1) additional regressor types (e.g., 1D convolutional neural networks); (2) new methods of spectral preprocessing; (3) moisture correction; and (4) dimensionality reduction (e.g., wavelets). Also incorporated is ancillary data representing terrain parameters. The target metric will consistently exceed RPIQ>2.0 and R2>0.8.

With respect to FIGS. 7 and 8, the spectroscopic probe contains a number of instruments, each of which produces its own data stream. The probe is inserted into the soil at a number of locations in the study site, often in a grid pattern. The probe insertions chosen for the training set are selected randomly from the population of the probe insertions at each site. Descriptive statistics are run to make sure there is nothing unusual about the division into training-validation-test sets. At each probe insertion location, the probe is inserted to its maximum insertion depth, and as it is inserted data from these instruments are recorded at regular intervals (e.g., every 2.5 cm) as the probe is inserted into the soil, so that each probe insertion produces an array of data from the instruments taken at different depths in the soil. GPS/GNSS: The GPS/GNSS instrument records the location of the probe insertion. Linear Encoder: The linear encoder measures the distance the probe has moved away from its fully retracted position, from which can be calculated the depth to which the probe has been inserted into the soil. Load Cell: The load cell measures the pressure as the probe is inserted into the soil. Spectrometers: There are two spectrometers that operate in different wavelength ranges: 400-1100 nm and 1100-2500 nm. The spectrometer readings from the soil are compared to readings from a white calibration blank, and are recorded as absorbance spectra. The data is saved to the hard drive of the computer running the device as it is collected. After each field day, can be uploaded and stored into a cloud-based database.

The models also utilize data derived from ancillary sources, in which data values for each probe insertion are extracted by matching the probe insertion location to the data value mapped at that location. Elevation: The elevation data, from public data sources (USGS Digital Elevation Models), are a grid of surface elevation measurements at each grid cell. The elevation data are used to derive a number of variables describing the topographic surface surrounding the probe's location. Variables can include elevation, slope, surface curvature, relative topographic position, and compound indices such as the topographic wetness index. Soil Survey Map: The soil survey map, from public data sources (Natural Resources Conservation Service soil surveys), is a grid of the mapped soil type at each location. The soil survey map is used to derive a number of variables describing the soil that has been mapped at the probe insertion location. Variables can include the mapped soil type, soil texture, parent material type, and other information included in the NRCS database associated with the soil map. Other Mapped Data: Other mapped data, such as variables derived from remotely sensed imagery, may also be included in the model.

A core of soil is sampled immediately adjacent to probe insertions. The core is divided into a number of depth increments (e.g., at 10 cm depth intervals). The core segments are analyzed in the lab for the soil property or properties of interest (e.g., organic carbon content, bulk density, and water content).

The soil core lab analyses represent the quantities that the machine learning model will predict. Thus they function as the measured values against which the model predictions will be evaluated. Each soil core segment is matched with the corresponding depth increments of the spectroscopic probe dataset, and with the ancillary data corresponding to the location of the probe insertion. The probe insertions are randomly divided into three sets: training (60%), validation (20%), and test (20%). The training set is used to create the model. The validation set is used for routine evaluation of the fit of the model when applied to data not used in training, and the test set is used to evaluate the fit of the final model choice when applied to data not used in any way during the training process.

The spectral data are highly multicollinear and need to undergo preprocessing before they are input into the model. This involves two separate steps. First the spectral variables are resampled to a wavelength interval longer than the spectrometer's native wavelength interval, thus reducing the number of variables input into the model. Within one spectrum, a linear interpolation is performed to an evenly spaced set of wavelengths from the irregularly spaced wavelengths that were measured. Then spectra are normalized on a spectrum-by-spectrum basis. The normalization algorithm is often the standard normal variate, in which the spectrum mean is subtracted from the spectrum, and that quantity is divided by the spectrum standard deviation. Alternatively, the normalization procedure can be a first derivative spectrum calculated using the Savitzky-Golay algorithm.

The preprocessed spectral data variables, the depth and insertion variables, and the ancillary variables are all standardized to a common scale by removing the mean and scaling to unit variance. Scale standardization is calculated independently on each variable. Scale standardization normalizes the spectra and other data over the entire training dataset by taking for each variable (e.g., each wavelength) the $z=(x-u)/s$ where u is the mean of the training samples and s is the standard deviation of the training samples.

At this point, there are a large number of variables, since even after resampling the dataset from each spectrometer represents hundreds of variables, many of them correlated with each other. We therefore reduce the number of variables by recursively considering smaller and smaller sets of variables using the Recursive Feature Elimination (RFE) algorithm with cross-validation and support vector regression.

Machine learning regressors include (1) partial least squares, (2) support vector machines, (3) random forest, (4) AdaBoost, and (5) one-dimensional convolutional neural networks. All possible combinations of spectral normalization, regressor, and regressor parameters are generated, evaluating each combination using five-fold cross validation. The best model at this stage of the search is the combination yielding the lowest root mean square error of cross-validation. High-performing models are then evaluated by calculating the root mean square error on the validation set. The final model choice is evaluated using the test set.

Non-limiting aspects have been described, hereinabove. It will be apparent to those skilled in the art that the above methods and apparatuses may incorporate changes and modifications without departing from the general scope of the present subject matter. It is intended to include all such modifications and alterations in so far as they come within the scope of the appended claims or the equivalents thereof.

Having thus described the present teachings, it is now claimed:

1. A method for mapping distribution of chemical compounds in soil, the method comprising the steps of:
    inserting a probe into the soil at multiple locations;
    utilizing a global navigation satellite system to record the locations of the probe;
    measuring a depth the probe was inserted into the soil for at least two of the multiple locations;
    measuring a pressure at which the probe was inserted into the soil for at least two of the multiple locations;
    obtaining spectroscopic data regarding the soil;
    determining at least one of the group consisting of elevation, slope, surface curvature, relative topographic position, and topographic wetness index of the soil;
    determining at least one of the group consisting of soil type, soil texture, and parent material type;
    sampling a core of soil adjacent to the probe locations;
    dividing the core into multiple depth increments;
    analyzing the core;
    matching each core with a corresponding depth increment of the probe insertions;
    obtaining probe insertion data from the probe insertions;
    dividing the probe insertion data into training, validation, and test categories;
    resampling spectral variables from the probe insertion data to a wavelength interval longer than a native wavelength interval of an associated spectrometer;
    normalizing the probe insertion data on a spectrum by spectrum basis, utilizing a machine learning normalization algorithm, wherein the machine learning normalization algorithm is either a standard normal variate or a Savitzky-Golay algorithm;
    standardizing the spectral variables to a common scale by removing a mean and scaling to unit variance;
    reducing the number of spectral variables using a Recursive Feature Elimination algorithm with cross-validation and support vector regression;
    generating all possible combinations of spectral normalization, regressors, and regressor parameters;
    evaluating each of the combinations using five-fold cross validation;
    choosing the combination yielding a lowest root mean square error of cross-validation; and
    choosing a model utilizing a test set.

2. A method for mapping distribution of chemical compounds in soil, the method comprising the steps of:
  inserting a probe into the soil at multiple locations;
  obtaining spectroscopic data regarding the soil;
  sampling a core of soil adjacent to the probe locations;
  dividing the core into multiple depth increments;
  analyzing the core;
  matching each core with a corresponding depth increment of the probe insertions;
  obtaining probe insertion data from the probe insertions;
  dividing the probe insertion data into training, validation, and test categories;
  resampling spectral variables from the probe insertion data to a wavelength interval longer than a native wavelength interval of an associated spectrometer;
  normalizing the probe insertion data on a spectrum by spectrum basis, utilizing a machine learning normalization algorithm;
  standardizing the spectral variables to a common scale by removing a mean and scaling to unit variance; and
  choosing a model utilizing a test set.

3. The method of claim 2, further comprising utilizing a global navigation satellite system to record the locations of the probe.

4. The method of claim 3, further comprising measuring a depth the probe was inserted into the soil for at least two of the multiple locations.

5. The method of claim 4, further comprising measuring a pressure at which the probe was inserted into the soil for at least two of the multiple locations.

6. The method of claim 5, further comprising determining at least one of the group consisting of elevation, slope, surface curvature, relative topographic position, and topographic wetness index of the soil.

7. The method of claim 6, further comprising determining at least one of the group consisting of soil type, soil texture, and parent material type.

8. The method of claim 7, further comprising reducing the number of spectral variables using a Recursive Feature Elimination algorithm with cross-validation and support vector regression.

9. The method of claim 8, further comprising generating all possible combinations of spectral normalization, regressors, and regressor parameters.

10. The method of claim 2, further comprising:
  generating all possible combinations of spectral normalization, regressors, and regressor parameters;
  evaluating each of the combinations using five-fold cross validation; and
  choosing the combination yielding a lowest root mean square error of cross-validation, wherein the machine learning normalization algorithm is either a standard normal variate or a Savitzky-Golay algorithm.

11. A non-transitory computer readable storage device storing computer executable instructions that when executed by a computer controls the computer to perform a method comprising:
  inserting a probe into soil at multiple locations;
  obtaining spectroscopic data regarding the soil;
  sampling a core of soil adjacent to the probe locations;
  dividing the core into multiple depth increments;
  analyzing the core;
  matching each core with a corresponding depth increment of the probe insertions;
  obtaining probe insertion data from the probe insertions;
  dividing the probe insertion data into training, validation, and test categories;
  resampling spectral variables from the probe insertion data to a wavelength interval longer than a native wavelength interval of an associated spectrometer;
  normalizing the probe insertion data on a spectrum by spectrum basis, utilizing a machine learning normalization algorithm;
  standardizing the spectral variables to a common scale by removing a mean and scaling to unit variance; and
  choosing a model utilizing a test set.

12. The non-transitory computer readable storage device of claim 11, further comprising utilizing a global navigation satellite system to record the locations of the probe.

13. The non-transitory computer readable storage device of claim 12, further comprising measuring a depth the probe was inserted into the soil for at least two of the multiple locations.

14. The non-transitory computer readable storage device of claim 13, further comprising measuring a pressure at which the probe was inserted into the soil for at least two of the multiple locations.

15. The non-transitory computer readable storage device of claim 14, further comprising determining at least one of the group consisting of elevation, slope, surface curvature, relative topographic position, and topographic wetness index of the soil.

16. The non-transitory computer readable storage device of claim 15, further comprising determining at least one of the group consisting of soil type, soil texture, and parent material type.

17. The non-transitory computer readable storage device of claim 16, further comprising reducing the number of spectral variables using a Recursive Feature Elimination algorithm with cross-validation and support vector regression.

18. The non-transitory computer readable storage device of claim 17, further comprising generating all possible combinations of spectral normalization, regressors, and regressor parameters.

19. The non-transitory computer readable storage device of claim 18, further comprising:
  evaluating each of the combinations using five-fold cross validation; and
  choosing the combination yielding a lowest root mean square error of cross-validation, wherein the machine learning normalization algorithm is either a standard normal variate or a Savitzky-Golay algorithm.

* * * * *